United States Patent
Model

(10) Patent No.: US 10,499,981 B2
(45) Date of Patent: *Dec. 10, 2019

(54) INTRAUTERINE TREATMENT DEVICE WITH ARTICULATING ARRAY

(71) Applicant: HOLOGIC, INC., Malborough, MA (US)

(72) Inventor: Jeffrey Model, Cambridge, MA (US)

(73) Assignee: Hologic, Inc., Marlborough, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/878,326

(22) Filed: Jan. 23, 2018

(65) Prior Publication Data
US 2018/0199989 A1    Jul. 19, 2018

Related U.S. Application Data

(63) Continuation of application No. 13/800,352, filed on Mar. 13, 2013, now Pat. No. 9,895,192.

(51) Int. Cl.
A61B 18/14    (2006.01)
A61B 17/42    (2006.01)
(Continued)

(52) U.S. Cl.
CPC .......... *A61B 18/1485* (2013.01); *A61B 17/42* (2013.01); *A61B 2017/00557* (2013.01);
(Continued)

(58) Field of Classification Search
CPC ........ A61B 18/1485; A61B 2018/0559; A61B 2018/0057; A61B 2019/2215; A61B 2019/465; A61B 17/42
(Continued)

(56) References Cited

U.S. PATENT DOCUMENTS 2,190,383 A    2/1940    Newman
4,489,732 A    12/1984   Hasson
(Continued)

FOREIGN PATENT DOCUMENTS

AU    2005319523    6/2006
CA    2591535       6/2006
(Continued)

OTHER PUBLICATIONS

Ole Daniel Emerson—Who Named It?, a description of Simpson's Uterine Sound (Sir James Young Simpson), <http://wvvw.whonamedit.com/synd.cfm/2993.html>, 1994-2001, 1 page.
(Continued)

*Primary Examiner* — Eric D. Bertram
*Assistant Examiner* — Pamela M. Bays
(74) *Attorney, Agent, or Firm* — Vista IP Law Group, LLP

(57) ABSTRACT

An intrauterine device includes an articulating array. The intrauterine device can be operated by articulating the articulating array into an installed position or geometry within the uterus of a patient. Further, the articulating array can be constructed to include an insertion geometry have a smaller cross section than an installation geometry. The articulating array can also be constructed to be housed within a sheath in the intrauterine device. Once the sheath has been inserted into a patient, for example through the patient's cervix, the articulating array can be deployed in its insertion geometry and then articulated into an installed position. The articulating array can include a plurality of expansion chambers. The expansion chambers can be constructed and arranged to take on the installed geometry when expanded. In one embodiment, the purpose of the articulating array is to position a conductive array within the patient's uterus enabling ablation of the uterine lining.

13 Claims, 10 Drawing Sheets

(51) Int. Cl.
*A61B 18/00* (2006.01)
*A61B 34/30* (2016.01)
*A61B 17/00* (2006.01)
*A61B 90/00* (2016.01)

(52) U.S. Cl.
CPC ............. *A61B 2017/4216* (2013.01); *A61B 2018/00559* (2013.01); *A61B 2018/00577* (2013.01); *A61B 2018/00791* (2013.01); *A61B 2034/302* (2016.02); *A61B 2090/065* (2016.02)

(58) Field of Classification Search
USPC .................................................. 606/41
See application file for complete search history.

(56) References Cited

U.S. PATENT DOCUMENTS

| | | | |
|---|---|---|---|
| 4,946,440 A | 8/1990 | Hall | |
| 5,002,558 A | 3/1991 | Klein et al. | |
| 5,188,596 A | 2/1993 | Condon et al. | |
| 5,217,466 A | 6/1993 | Hasson | |
| 5,235,966 A | 8/1993 | Jamner | |
| 5,314,443 A | 5/1994 | Rudnick | |
| 5,501,681 A | 3/1996 | Neuwirth et al. | |
| 5,542,928 A | 8/1996 | Evans et al. | |
| 5,656,013 A * | 8/1997 | Yoon ............... | A61B 17/00234 600/207 |
| 5,702,438 A | 12/1997 | Avitall | |
| 5,769,880 A | 6/1998 | Truckai et al. | |
| 5,800,493 A * | 9/1998 | Stevens ................ | A61B 18/08 606/28 |
| 5,830,179 A | 11/1998 | Mikus et al. | |
| 5,882,290 A | 3/1999 | Kume | |
| 5,891,094 A | 4/1999 | Masterson et al. | |
| 5,935,098 A | 8/1999 | Blaisdell et al. | |
| 6,096,047 A | 8/2000 | Smit | |
| 6,159,207 A | 12/2000 | Yoon | |
| 6,261,219 B1 | 7/2001 | Meloul et al. | |
| 6,266,568 B1 * | 7/2001 | Mann .................. | A61N 1/0541 607/137 |
| 6,277,089 B1 | 8/2001 | Yoon | |
| 6,450,977 B1 | 9/2002 | Baxter-Jones | |
| 6,450,983 B1 | 9/2002 | Rambo | |
| 6,468,292 B1 | 10/2002 | Mollenauer et al. | |
| 6,540,655 B1 | 4/2003 | Chin et al. | |
| 6,547,784 B1 | 4/2003 | Thompson et al. | |
| 6,607,477 B1 | 8/2003 | Longton et al. | |
| 6,607,545 B2 | 8/2003 | Kammerer et al. | |
| 6,635,054 B2 | 10/2003 | Fjield et al. | |
| 6,663,626 B2 | 12/2003 | Truckai et al. | |
| 6,706,026 B1 | 3/2004 | Goldstein et al. | |
| 6,796,976 B1 | 9/2004 | Chin et al. | |
| 6,813,520 B2 | 11/2004 | Truckai et al. | |
| 6,840,937 B2 | 1/2005 | Van Wyk | |
| 6,929,642 B2 | 8/2005 | Xiao et al. | |
| 6,942,648 B2 | 9/2005 | Schaible et al. | |
| 6,960,203 B2 | 11/2005 | Xiao et al. | |
| 7,101,367 B2 | 9/2006 | Xiao et al. | |
| 7,105,007 B2 | 9/2006 | Hibler | |
| 7,381,208 B2 | 6/2008 | van der Walt et al. | |
| 7,500,973 B2 | 3/2009 | Vancelette et al. | |
| 7,625,368 B2 | 12/2009 | Schechter et al. | |
| 7,674,259 B2 | 3/2010 | Shadduck | |
| 7,963,962 B2 | 6/2011 | Thompson et al. | |
| 8,007,449 B2 | 8/2011 | Kotmel et al. | |
| 8,025,656 B2 | 9/2011 | Gruber et al. | |
| 8,298,213 B2 | 10/2012 | Singh | |
| 8,348,864 B2 | 1/2013 | Kotmel et al. | |
| 8,372,068 B2 | 2/2013 | Truckai | |
| 8,597,289 B2 | 12/2013 | Layton, Jr. et al. | |
| 2002/0022832 A1 | 2/2002 | Mikus et al. | |
| 2002/0058951 A1 | 5/2002 | Fiedler | |
| 2002/0068934 A1 | 6/2002 | Edwards et al. | |
| 2002/0082667 A1 | 6/2002 | Shadduck | |
| 2002/0177846 A1 | 11/2002 | Mulier et al. | |
| 2002/0183730 A1 | 12/2002 | Reu et al. | |
| 2004/0002698 A1 | 1/2004 | Hua Xiao et al. | |
| 2004/0098013 A1 | 5/2004 | Ciaglia et al. | |
| 2004/0122463 A1 | 6/2004 | Hibler | |
| 2005/0061329 A1 | 3/2005 | Tran et al. | |
| 2005/0085827 A1 | 4/2005 | G. et al. | |
| 2005/0085880 A1 * | 4/2005 | Truckai .............. | A61B 18/1485 607/101 |
| 2005/0159644 A1 | 7/2005 | Takano | |
| 2005/0209627 A1 | 9/2005 | Kick et al. | |
| 2005/0234543 A1 | 10/2005 | Glaser et al. | |
| 2005/0283178 A1 | 12/2005 | Flagle et al. | |
| 2006/0004398 A1 | 1/2006 | Binder et al. | |
| 2006/0047269 A1 | 3/2006 | Reever et al. | |
| 2006/0135887 A1 | 6/2006 | Sampson et al. | |
| 2006/0200185 A1 | 9/2006 | Marchek et al. | |
| 2006/0212062 A1 | 9/2006 | Farascioni | |
| 2006/0271034 A1 | 11/2006 | Swanson | |
| 2007/0005089 A1 | 1/2007 | Smith et al. | |
| 2007/0032814 A1 | 2/2007 | Hibler | |
| 2007/0066990 A1 | 3/2007 | Marsella et al. | |
| 2007/0142752 A1 | 6/2007 | Kotmel et al. | |
| 2008/0039864 A1 | 2/2008 | Feuer et al. | |
| 2008/0039865 A1 | 2/2008 | Shaher et al. | |
| 2008/0109010 A1 | 5/2008 | Feuer et al. | |
| 2008/0135053 A1 | 6/2008 | Gruber et al. | |
| 2008/0208189 A1 | 8/2008 | Van Wyk et al. | |
| 2008/0245374 A1 | 10/2008 | Agnew | |
| 2008/0249534 A1 | 10/2008 | Gruber et al. | |
| 2008/0259730 A1 | 10/2008 | Di Federico | |
| 2008/0312644 A1 | 12/2008 | Fourkas et al. | |
| 2009/0054868 A1 | 2/2009 | Sharkey et al. | |
| 2009/0054870 A1 | 2/2009 | Sharkey et al. | |
| 2009/0062602 A1 | 3/2009 | Rosenberg et al. | |
| 2009/0125010 A1 | 5/2009 | Sharkey et al. | |
| 2009/0137970 A1 | 5/2009 | George et al. | |
| 2009/0149846 A1 | 6/2009 | Hoey et al. | |
| 2009/0270989 A1 | 10/2009 | Conner et al. | |
| 2009/0292307 A1 | 11/2009 | Razzack | |
| 2009/0306588 A1 | 12/2009 | Nguyen et al. | |
| 2010/0004651 A1 | 1/2010 | Biyani | |
| 2010/0094074 A1 | 4/2010 | Mark et al. | |
| 2010/0094075 A1 | 4/2010 | Mark | |
| 2010/0100091 A1 | 4/2010 | Truckai | |
| 2010/0114089 A1 | 5/2010 | Truckai et al. | |
| 2010/0114147 A1 | 5/2010 | Biyani | |
| 2010/0228239 A1 | 9/2010 | Freed | |
| 2010/0256623 A1 | 10/2010 | Nicolas et al. | |
| 2010/0268244 A1 | 10/2010 | Hansen et al. | |
| 2010/0274260 A1 | 10/2010 | D'Arpiany et al. | |
| 2011/0160715 A1 | 6/2011 | Ostrovsky et al. | |
| 2011/0190783 A1 | 8/2011 | Calderon | |
| 2011/0208178 A1 | 8/2011 | Truckai | |
| 2011/0213231 A1 | 9/2011 | Hall et al. | |
| 2012/0065632 A1 | 3/2012 | Shadduck | |
| 2012/0101332 A1 | 4/2012 | Truckai et al. | |
| 2012/0116378 A1 | 5/2012 | Toth et al. | |
| 2012/0209281 A1 | 8/2012 | Truckai | |
| 2012/0245581 A1 | 9/2012 | Truckai | |
| 2013/0206147 A1 | 8/2013 | Skalyni | |
| 2013/0269705 A1 | 10/2013 | Kochem et al. | |
| 2014/0200591 A1 | 7/2014 | Sullivan et al. | |
| 2014/0216467 A1 | 8/2014 | Kochem et al. | |
| 2014/0276234 A1 | 9/2014 | Hines et al. | |

FOREIGN PATENT DOCUMENTS

| | | |
|---|---|---|
| EP | 1827231 | 9/2007 |
| WO | WO 2006/068807 | 6/2006 |
| WO | WO 2010053700 | 5/2010 |
| WO | WO 2011084616 | 7/2011 |

OTHER PUBLICATIONS

Pelican Healthcare Ltd., "Pelican Disposable Uterine Sound—Sterile", Product Description, <http://www.pelicanhealthcare.co.uk/sound.htm>, undated, accessed on Mar. 31, 2005, 1 page.

(56) References Cited

OTHER PUBLICATIONS

Pelican Healthcare Ltd., "Pelican Disposable Sound—Technical Data Sheet", <http://wvvw.pelicanhealthcare.co.uk/ pdfs/sound.pft>, undated, accessed on Mar. 31, 2005,1 page.
Westons Internet Sales, "Uterine Sound", various products, <http://www.westons.com/acatalog/Online_Catalogue_Uterine_sound_326.html>, last modified Feb. 23, 2005, 2 pages.
Track of Surgical, "Assorted Uterine Sounds", various products, <http://www.track.com.pk/assorted2.htm>, undated—last printed Mar. 31, 2005, 2 pages.
Life Care Supplies, "OB/GYN Instruments—Sklar Surgical Instruments—Uterine Sounds", various products, <http:// lcsupplies.com/products/obgyn/sound.htm>, undated—downloaded on Mar. 31, 2005, 1 page.
Gilbert Surgical Instruments, "Sounds", various products, <http://www.gilbertsurgical.com/html/fm/sounds.html>, 2000, 1 page.
Notification of Transmittal of the International Search Report and the Written Opinion of the International Searching Authority, or the Declaration for International Application No. PCT/US13/60613, dated Dec. 12, 2013, 19 pages.
Shepherd et al. 10.1073/pnas-1116564108_ SI(2)—Supporting Information—pp. 1-7; Mar. 8, 2013.
International Search Report issued in corresponding International Application No. PCT/US2013/606113, dated Dec. 12, 2013.
International Search Report issued in corresponding International Application No. PCT/US2014/014895, dated Mar. 27, 2014.
International Search Report issued in corresponding International Application No. PCT/US2014/014544, dated Jun. 10, 2014, 3 pages.

* cited by examiner

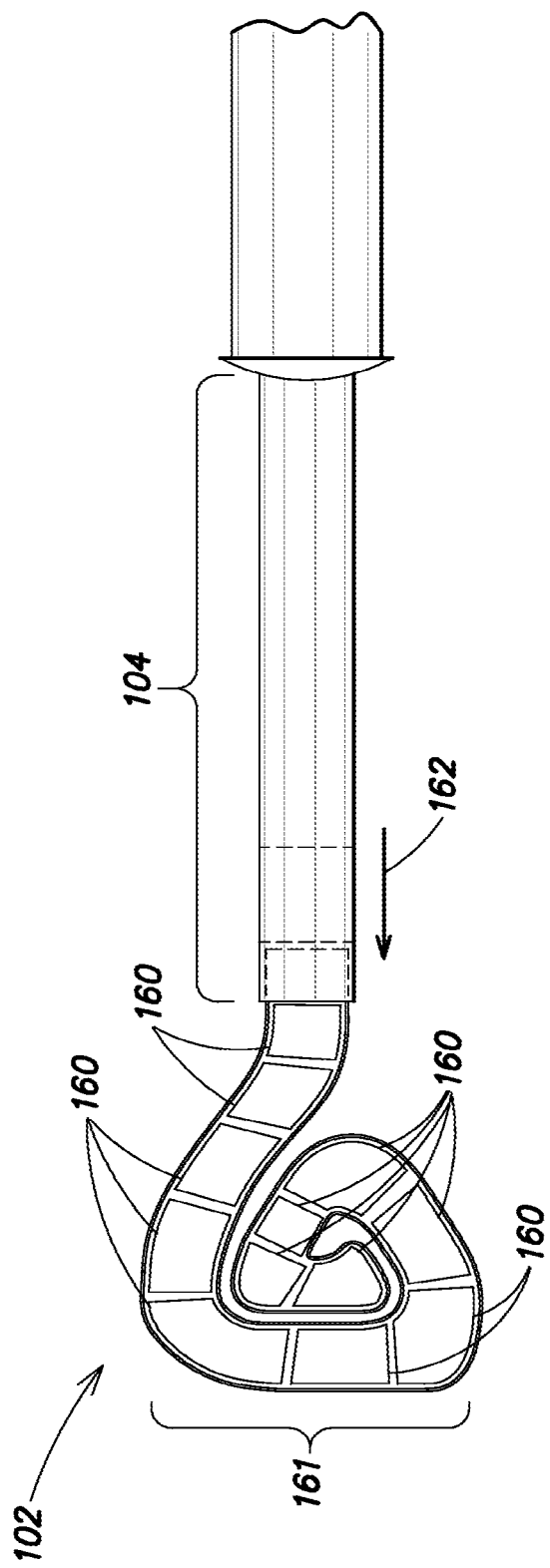

INTRAUTERINE TREATMENT DEVICE WITH ARTICULATING ARRAY

RELATED APPLICATION DATA

The present application is a continuation of U.S. patent application Ser. No. 13/800,352, filed Mar. 13, 2013, now issued as U.S. Pat. No. 9,895,192, the priority of which is claimed under 35 U.S.C. § 120, and the contents of which is incorporated herein by reference in its entirety, as though set forth in full.

BACKGROUND

Intrauterine medical devices are often inserted through a patient's cervix and then expanded inside the patient's uterus. For example, a uterine ablation procedure may be performed by inserting a medical device having a sheath through the cervix and then extending an ablation device through the distal end of the sheath and expanding the ablation device in the uterus. The ablation device can be expanded inside the patient, out of view of the person performing the procedure. Deployment of such medical devices and/or ablation devices and their subsequent robustness can be important to avoid complications and potential injury to the patient during a procedure.

SUMMARY

Conventional intrauterine medical devices employed, for example, for uterine ablation oftentimes rely on expanding a rigid structure inside a patient into a fixed geometry. It is realized that the ability to position such conventional devices can be limited by the structure of the device itself, and additionally the ability to conform to the intended area inside the patient can likewise be limited. Further, rigid portions of such conventional devices present perforation risk to the patient undergoing the procedure, where the structures of the treatment device cause internal wounds or perforations during the procedure.

Accordingly, provided are flexible intrauterine medical devices having soft articulating arrays. The articulating arrays can include a plurality of chambers that when expanded cause the articulating array to transition into an installed position, for example, within the uterus of the patient. In some embodiments, the plurality of chambers can be configured to transition between an insertion geometry and an installed geometry, where the insertion geometry is configured to have a small cross section relative to the installed geometry. The soft articulating arrays can be advantageous because the soft articulating array has no rigid structures to increase perforation risk. Furthermore the smaller insertion geometry can permit intrauterine devices having smaller cross sections, which can reduce difficulty in insertion and reduce patient discomfort during such procedures. The soft articulating arrays can be articulated from an insertion geometry into an installed position by, for example, inflating a plurality of chambers within the articulating array. Selective and/or controlled inflation of the plurality of chambers can cause the articulating array to take on a variety of geometries for the installed positions. In some embodiments, the articulating array can reach a roughly triangular geometry once in an installed position/geometry.

In some embodiments, the articulation of the articulating array into the installed position can enable greater intimate contact over a larger surface area within the patient over some conventional devices. The greater contacting surface area can improve robustness of the positioning of the device during any procedure. Further aspects and embodiment are directed to reducing the diameter of the sheath used in conjunction with the articulating array of an intrauterine device while maintaining the strength and robustness of the device. Reducing the diameter of the sheath of an intrauterine device improves its ease of insertion and decreases patient discomfort.

According to one aspect, an intrauterine device is provided. The intrauterine device comprises a sheath, an articulating array disposed within the sheath during insertion of the intrauterine device, wherein the articulating array includes a plurality of expansion chambers, an insertion geometry maintained when the plurality of expansion chambers are in a non-expanded position, and an installed geometry maintained when the plurality of expansion chambers are in an expanded position, and a conductive array on a surface of the articulating array, wherein the conductive array is configured to ablate a uterine surface upon receiving input power.

According to some embodiments, the intrauterine device further comprises an RF generator configured to supply power to the conductive array. In another embodiment, the conductive array is disposed on an exterior surface of the articulating array. In another embodiment, the conductive array is constructed and arranged to ablate the uterine surface when the articulating array is configured in the installed geometry.

In another embodiment, the articulating array further comprises a plurality of channels connected to the plurality of expansion chambers for controlling pressure within the plurality of expansion chambers. In another embodiment, the intrauterine device further comprises a pressure controller configured to increase or decrease pressure in the plurality of expansion chambers. In another embodiment, the articulating array transitions between the insertion geometry and the installed geometry responsive to increased pressure delivered by the pressure controller. In another embodiment, the articulating array transitions between the installation geometry and the insertion geometry responsive to decreased pressure in the plurality of expansion chambers. In another embodiment, the pressure controller is configured to alter pressure in the plurality of expansion chambers in response to physical manipulation. In another embodiment, the pressure controller is configured to operate a pump to increase pressure in the plurality of expansion chambers. In another embodiment, the plurality of expansion chambers are constructed and arranged of high elongation silicone. In another embodiment, the articulating array is constructed and arranged of a flexible material having a plurality of elasticities.

In another embodiment, the articulating array further comprises the at least one sensor for establishing position of the articulating array. In another embodiment, the at least one sensor includes a contact sensor on an exterior portion of the articulating application while the articulating array is in the installed geometry. In another embodiment, the at least one sensor includes a strain gauge.

According to one aspect, an intrauterine device is provided. The intrauterine device comprises an articulating array, wherein the articulating array includes a plurality of expansion chambers, an insertion geometry maintained when the plurality of expansion chambers are in a non-expanded position, and an installed geometry maintained when the plurality of expansion chambers are in an expanded position, and a conductive array on a surface of the articulating array, configured to ablate a uterine surface upon receiving input power.

In one embodiment, the intrauterine device further comprises a sheath configured to enclose the articulating array. In another embodiment, the intrauterine device further comprises a controller configured to transition the articulating array between the installed geometry and the insertion geometry. In another embodiment, the intrauterine device further comprises wherein a cross section of the installed geometry defines a substantially triangular shape. In another embodiment, the conductive array is constructed and arranged of at least one electrode array on the surface of the articulating array.

According to one aspect, an intrauterine ablation device is provided. The intrauterine device comprises an articulating array including a plurality of expansion chambers that provides an insertion geometry of the articulating array when the plurality of expansion chambers are in a non-expanded position, and that provides an installed geometry of the articulating array when the plurality of expansion chambers are in an expanded position, and a conductive array disposed on a surface of the articulating array that is configured, in response to receiving an input power, to provide a signal to ablate a uterine surface when the articulating array is in the installed geometry.

In one embodiment, the intrauterine device further comprises an RF generator configured to supply the input power to the conductive array. In another embodiment, the conductive array is disposed on an exterior surface of the articulating array. In another embodiment, the conductive array comprises a plurality of electrodes arranged on the surface of the articulating array. In another embodiment, the conductive array is a conductive array supported by the articulating array. In another embodiment, the articulating array further comprises a plurality of channels coupled to the plurality of expansion chambers for controlling pressure within the plurality of expansion chambers.

In another embodiment, the intrauterine device further comprises a pressure controller coupled to the plurality of channels and configured to increase or decrease pressure in the plurality of expansion chambers. In another embodiment, the articulating array is configured to transition between the insertion geometry and the installed geometry responsive to increased pressure provided to the plurality of expansion chambers. In another embodiment, the articulating array is configured to transition between the installation geometry and the insertion geometry responsive to decreased pressure provided to the plurality of expansion chambers. In another embodiment, the pressure controller comprises a pump to increase pressure in the plurality of expansion chambers.

In another embodiment, the plurality of expansion chambers are constructed and arranged of high elongation silicone. In another embodiment, the articulating array is constructed and arranged of a flexible material having a plurality of elasticities. In another embodiment, the articulating array further comprises at least one sensor for sensing a position of the articulating array. In another embodiment, the at least one sensor includes a contact sensor on an exterior portion of the articulating array that senses a position of the articulating array while the articulating array in the installed geometry. In another embodiment, the at least one sensor includes a strain gauge. In another embodiment, the intrauterine device further comprises a sheath configured to enclose the articulating array and the conductive array.

In another embodiment, the intrauterine device further comprises a controller configured to control the pressure within the plurality of expansion chambers so as to transition the articulating array between the installed geometry and the insertion geometry. In another embodiment, a cross section of the installed geometry defines a substantially triangular shape.

According to another aspect, a method for facilitating ablation of a uterine tissue is provided. The method comprises providing an articulating array and a conductive array on a surface of the articulating array, advancing the articulating array and conductive array in an insertion geometry through a cervix canal and into a uterus of a patient, and transitioning the articulating array and the conductive array between the insertion geometry and an installed geometry, providing an input power to the conductive array so as to provide a signal to ablate a uterine surface with the articulating array in the installed geometry.

In one embodiment, the act of transitioning the articulating array and the conductive array includes an act of providing increased pressure to the plurality of expansion chambers. In one embodiment, the act of transitioning the articulating array and the conductive array includes an act of providing decreased pressure to the plurality of expansion chambers. In one embodiment, the articulating array and the conductive array are housed within a sheath, and the act of advancing the articulating array and the conductive array occurs while housed within the sheath. In one embodiment, the method further comprises an act of extending the articulating array and the conductive array from the sheath into the uterus of the patient.

In one embodiment, the method further comprises an act of generating the input power with an RF generator coupled to the conductive array. In one embodiment, the method further comprises an act of controlling pressure provided to the plurality of expansion chambers through a plurality of channels coupled to the plurality of expansion chambers. In one embodiment, the method further comprises an act of receiving sensor data from at least one sensor for sensing a position of the articulating array. In one embodiment, the method further comprises an act of altering pressure delivered to at least one of the plurality of expansion chambers responsive to the act of receiving sensor data from the at least one sensor.

According to one aspect an intrauterine ablation device is provided. The device comprises a sheath, an articulating array disposed within the sheath and including a plurality of expansion chambers to provide an insertion geometry of the articulating array when the plurality of expansion chambers are in a non-expanded position, and to provide an installed geometry of the articulating array when the plurality of expansion chambers are in an expanded position, a conductive array disposed on a surface of the articulating array and configured to receive an input signal, wherein the articulating array is configured to extend from the sheath and to retain the insertion geometry with the plurality of expansion chambers in the non-expanded position; and wherein the plurality of expansion chambers are configured to expand to transition to the installed geometry and the conductive array is configured, in response to receiving an input signal, to provide a signal to ablate a uterine surface with the articulating array in the installed geometry.

According to one embodiment, the plurality of expansion chambers are arranged in a linear arrangement configured to provide the insertion geometry. According to one embodiment, the conductive array is a conductive array supported by the articulating array. According to one embodiment, the articulating array further comprises a plurality of channels coupled to the plurality of expansion chambers for controlling pressure within the plurality of expansion chambers. According to one embodiment, the device further comprises a pressure controller coupled to the plurality of channels and configured to increase or decrease pressure in the plurality of expansion chambers.

According to one embodiment, the articulating array is responsive to changes in pressure within the plurality of expansion chambers such that the plurality of expansion chambers transition between the insertion geometry and the installed geometry. According to one embodiment, the articulating array further comprises at least one sensor for sensing a position of the articulating array. According to one embodiment, the at least one sensor includes a contact sensor on an exterior portion of the articulating array that is configured to sense a position of the articulating array while the articulating array is in the installed geometry.

According to one embodiment, the at least one sensor includes a strain gauge. According to one embodiment, the articulating array further comprising a controller configured to control the pressure within the plurality of expansion chambers so as to transition the articulating array between the installed geometry and the insertion geometry.

According to one aspect an intrauterine ablation device is provided. The device comprises a sheath, an articulating array disposed within the sheath and including a plurality of expansion chambers to provide an insertion geometry of the articulating array when the plurality of expansion chambers are in a non-expanded position, and to provide an installed geometry of the articulating array when the plurality of expansion chambers are in an expanded position, wherein the articulating array is configured to extend from the sheath and to retain the insertion geometry with the plurality of expansion chambers in the non-expanded position, and wherein the plurality of expansion chambers are configured to expand to transition to the installed geometry placing an outer surface of the articulating array proximate to a uterine lining of a patient.

According to one embodiment, the articulating array includes a delivery component for passing fluid proximate to the uterine lining to ablate the uterine lining. According to one embodiment, the device further comprises a controller configured to control the pressure within the plurality of expansion chambers so as to transition the articulating array between the installed geometry and the insertion geometry.

According to one aspect a method for facilitating ablation of a uterine tissue is provided. The method comprises providing an articulating array disposed within a sheath having a plurality of adjacent expansion chambers arranged in a linear arrangement, the articulating array having an insertion geometry with the plurality of expansion chambers in a non-expanded position and having an installed geometry with the plurality of expansion chambers in an expanded position, advancing the sheath and articulating array in the insertion geometry through a cervical canal and into a uterus of a patient, extending the articulating array from the sheath while maintaining the plurality of expansion chambers in the insertion geometry, expanding the plurality of expansion chambers to an expanded position so as to transition the articulating array and the conductive array between the insertion geometry and the installed geometry, and executing an ablation operation so as to ablate a uterine surface of the patient with the articulating array in the installed geometry.

According to one embodiment, the articulating array includes a conductive array disposed on a surface of the articulating array, and executing an ablation operation includes providing an input signal to the conductive array so as to ablate a uterine surface of the patient with the articulating array in the installed geometry. According to one embodiment, maintaining the plurality of expansion chambers in the insertion geometry includes selectively controlling pressure in the plurality of adjacent expansion chambers. According to one embodiment, expanding the plurality of adjacent expansion chambers includes expanding a first one of the plurality of expansion chambers such that a positioning of subsequent ones of the plurality of adjacent expansion chambers is modified.

According to one embodiment, the method further comprises an act of controlling pressure provided to the plurality of expansion chambers through a plurality of channels coupled to the plurality of expansion chambers. According to one embodiment, the method further comprises an act of receiving sensor data from at least one sensor for sensing a position of the articulating array. According to one embodiment, the method further comprises an act of altering pressure delivered to at least one of the plurality of expansion chambers responsive to the act of receiving sensor data from the at least one sensor.

Still other aspects, embodiments, and advantages of these exemplary aspects and embodiments, are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 3B is an elevation view of an embodiment of an intrauterine therapy application device with an articulating array in a deployed position, according to aspects of the disclosure;

DETAILED DESCRIPTION

Figure 1:
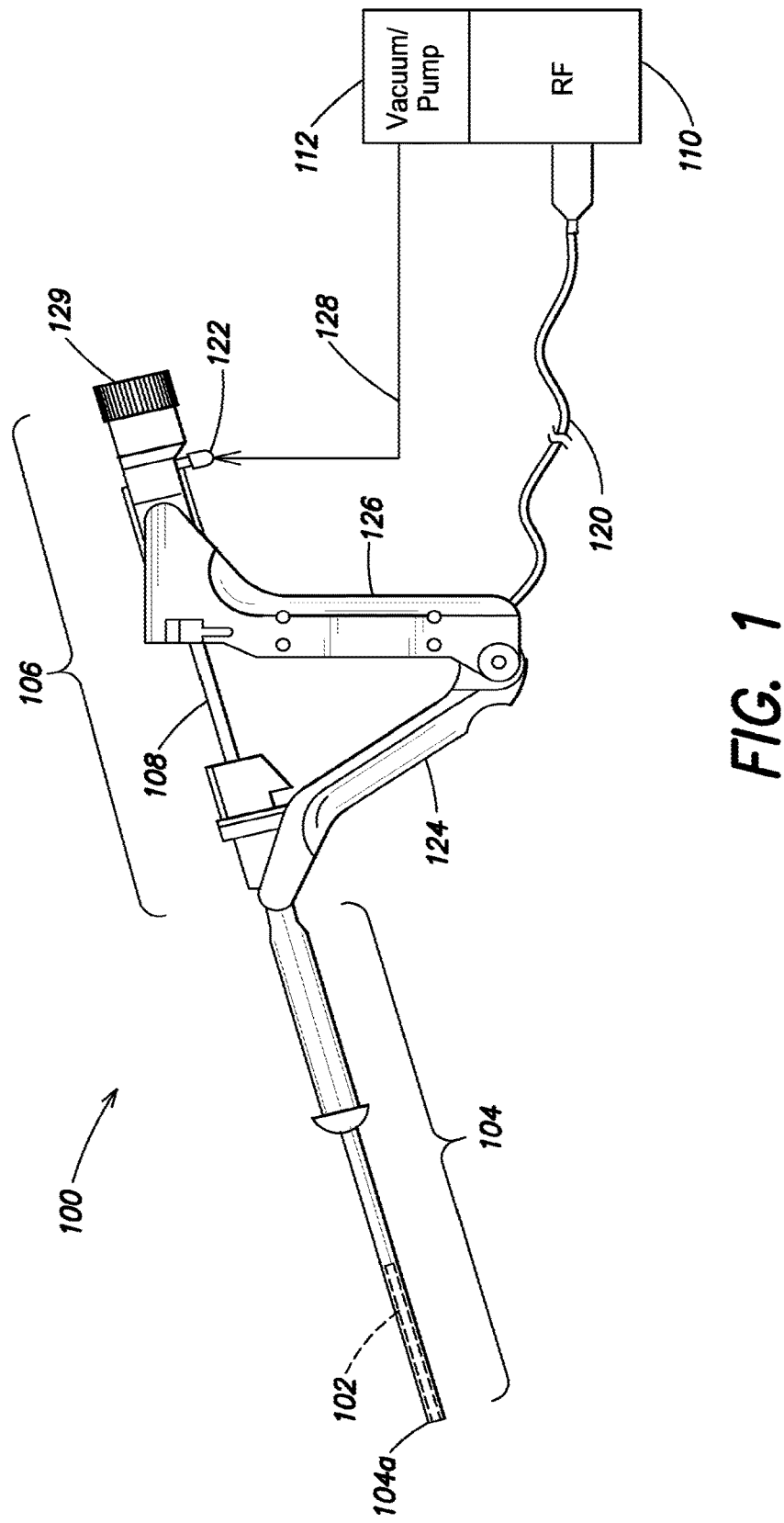
FIG. 1 is a side elevation view of an intrauterine therapy application device with an articulating array according to aspects of the disclosure.

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure.

According to aspects of this disclosure, various structures and methods are provided herein for decreasing a size or diameter of an intrauterine therapy application device in an insertion and/or retracted position, while maintaining its strength and robustness in expanded and/or deployed positions. Further, according to some aspects of the disclosure the structures and methods provide for more intimate contact between the device in an installed geometry and a patient's target cavity reducing, for example, risk of internal perforation during a medical procedure, including, for example, uterine ablation. In at least one embodiment, various structures and methods are provided for maintaining the robustness of a deployment mechanism of an intrauterine therapy application device by employing an articulating soft array.

Articulating arrays as discussed herein include a plurality of expansion chambers that can be inflated or deflated to provide one or more positions of the articulating array. In some embodiments, the articulating array is constructed of a soft extensible material having a plurality of expansion chambers. During insertion the articulating array maintains a small area, cross section, and/or diameter. Once inserted the articulating array can transition from an insertion geometry into an installed position that provides for intimate contact over the surface of the area within the patient being operated on by expanding the expansion chambers.

According to aspects of this disclosure, structures and methods are provided to decrease the stiffness of the installed device and provide for improved contact between, for example, the uterine lining and the installed geometry formed by the articulating array included in an intrauterine therapy application device. Among others, one advantage of employing an articulating array is the resulting decrease in the cross section of the intrauterine device, reducing patient discomfort and/or improving ease of insertion into an installed position within a patient. Accordingly, intrauterine devices are provided having a reduced size or diameter in collapsed or retracted position which enable a smaller-diameter sheath while still maintaining the deployment mechanism's robustness in both collapsed and deployed positions. Another advantage in a smaller outer diameter sheath includes reducing patient discomfort and decreasing the potential for cervical injury during insertion into the uterus. Further advantages can include the use of soft materials including, for example, silicone to fabricate the articulating arrays of the intrauterine therapy application device. Employing soft and/or flexible materials to construct the articulating arrays can reduce perforation risk in patients undergoing treatment.

In some embodiments, the articulating array can be housed within a sheath that is inserted into a patient. The articulating array or array component can be extended from the sheath in an insertion geometry. The insertion geometry can be configured to minimize the area, cross section, and/or diameter or the articulating array (and the corresponding sheath) to provide, for example, for patient comfort. The articulating array can then be transitioned from the insertion geometry into an installed geometry. The installed geometry is configured to have as much intimate contact with the patient's internals as is possible. The articulating array can be constructed with a conductive array configured to ablate, for example, the patient's uterine lining during an ablation procedure once the articulating array is in an installed position. Reference to a conductive array herein is intended to include an array of conductors disposed on the surface of an articulating, an array of conductors in the form of a mesh structure that can also be disposed on the surface of or within an articulating array. Additionally, reference to a conductive array is intended to include the examples of mesh arrays described in U.S. Pat. No. 6,813,520 to Truckai et al., which is hereby incorporated by reference herein in its entirety. In some embodiments, the articulating array can position a conductive array disposed on its surface, and in others be configured to deploy conductive array including a mesh structure of conductors into a position for ablation.

By way of introduction and referring to the Figures, illustrated in FIG. 1 is an intrauterine therapy application device including an articulating array 102, a sheath 104, and an RF generator 110. According to one embodiment, the sheath of the device is inserted through the patient's cervix. The articulating array may be retracted in a collapsed or retracted position within the sheath for insertion into the patient's cervix. The sheath may be inserted through the patient's cervix, and when the distal end 104A of the sheath is inside the uterus, the articulating array may be extended into the uterus in an insertion geometry and articulated into a deployed state or installed geometry in the uterus. FIG. 3B illustrates an intrauterine therapy application device array 102 in a deployed or installed position. Decreasing the size, such as the cross section of an insertion geometry of the articulating array, allows for use of a smaller-diameter sheath 104. A sheath having a smaller outer diameter may reduce patient discomfort, and also decrease the potential for cervical injury during insertion through the cervix and into the uterus.

Figure 3A:
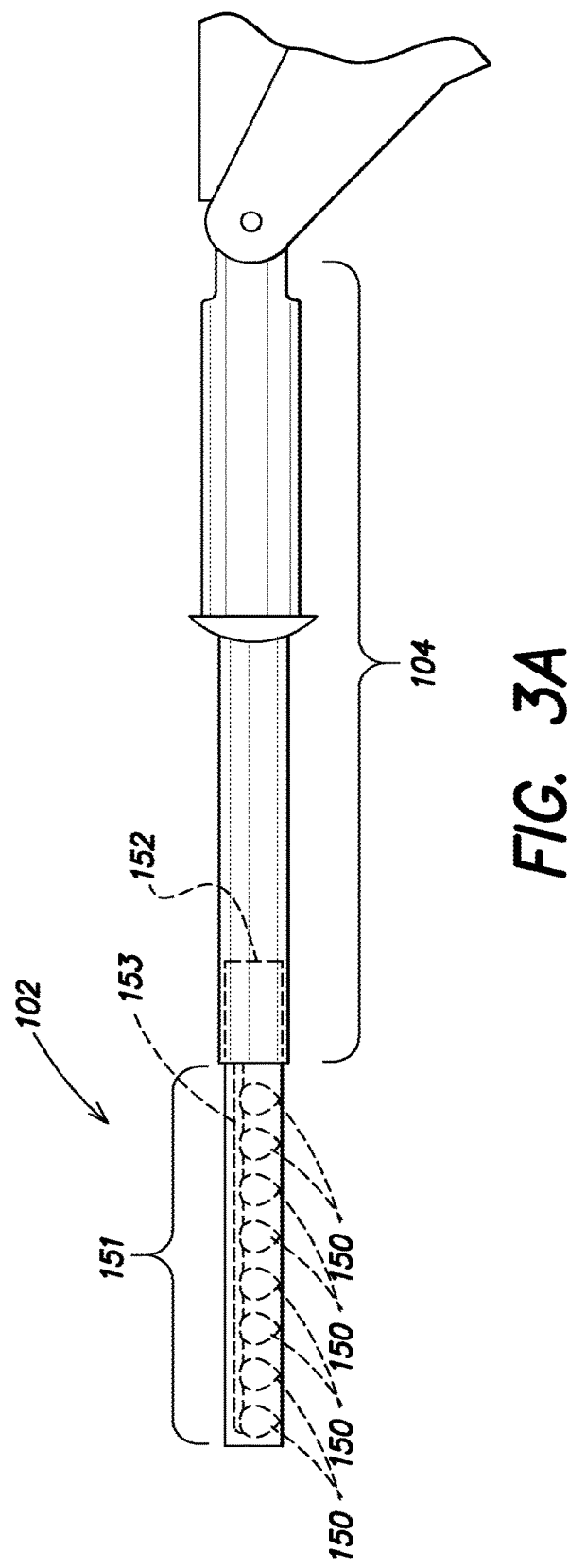
FIG. 3A is a perspective view of an embodiment of an intrauterine therapy application device with an articulating array in a deployed position, according to aspects of the disclosure.

In some embodiments, the device array 102 includes an articulating array, having a plurality of chambers (see e.g., 150 of FIG. 3A). In an insertion geometry or collapsed position, device array 102 is constructed and arranged to have a cylindrical structure shown, for example, in FIG. 3A. The plurality of chambers at 150 can be, for example, air chambers constructed and arranged to configure array 102 into an insertion geometry when the air chambers are under atmospheric air pressure, or in other words, when the air chambers are not inflated. Upon inflation, the air chambers can be configured to articulate the device array 102 into an installed geometry. In some embodiments, the installed geometry can be defined by the respective elasticities of the plurality of chambers and surrounding material. Using, for example, materials having a first elasticity for one wall of the plurality of chambers and materials having a greater elasticity for another wall of the plurality of chambers results in material having the greater elasticity distending to a greater extent than material having a lesser elasticity. This property can be configured to achieve a variety of geometries in any articulating array. In other embodiments, various sections, portions, etc., of an articulating array can be constructed to have a plurality of elasticities, permitting articulation into any one or more of triangular, square, elliptical, ovular, and spherical shapes, among other examples.

In some embodiments, the articulating array is constructed and arranged of a soft expandable material. For example, high expansion silicon can be used to fabricate the articulating array using known approaches. The articulating array can be fabricated to include a plurality of chambers, and channels within the articulating array, where the channels are used to control the expansion of the plurality of chambers (e.g., each array can include a plurality of chambers and a plurality of channels to introduce air or fluid into one or more chambers thereby controlling the expansion of the plurality of chambers). According to some embodiments, the articulating array can be constructed to have any of a variety of insertion geometries and articulate into any of a variety of installation geometries. In some embodiments, the insertion geometry includes a cylinder, so that the cross section of, for example, array 102 is minimized.

Figure 3C:
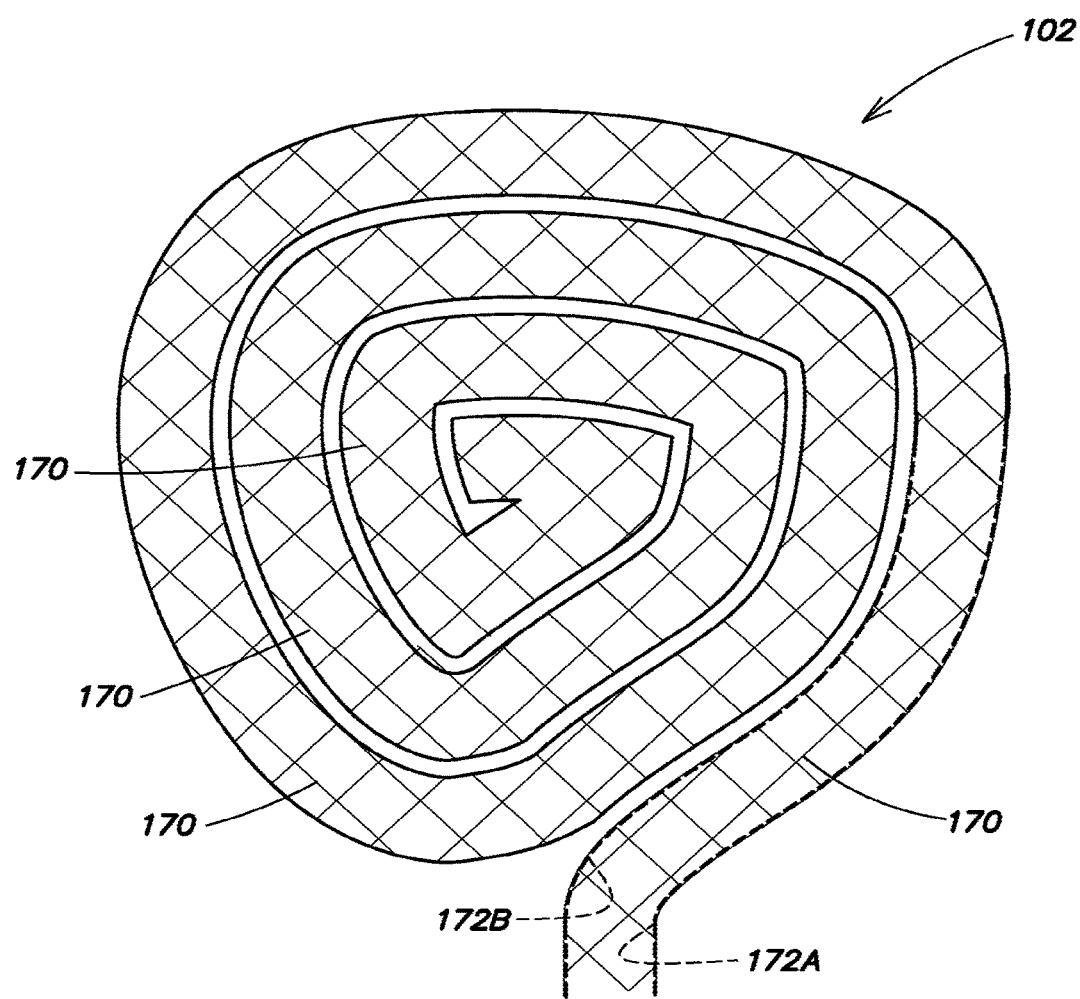
FIG. 3C is a perspective view of an embodiment of a portion of an intrauterine therapy application device with an articulating array showing a conductive array according to aspects of the disclosure.

In some further embodiments, the installed geometry of the articulating array includes a substantially triangular geometry to conform to patient physiology during an intrauterine procedure. In one example, the triangular geometry of the articulating array in its installed position enables deployment of a conductive array within a patient. The conductive array can be integrated on the outside of the articulating array (FIG. 3C, discussed in greater detail below). In some embodiments, the conductive array can be constructed and arranged on the surface of the articulating array, so that the conductive array is proximate to an ablation surface when the articulating array is in an installed position.

By releasing pressure on the plurality of chambers the articulating array can be configured to return to its insertion geometry, facilitating retraction of the articulating array from the patient and/or into the sheath.

Referring to FIG. 3A, the intrauterine therapy application device 100 can be deployed from the sheath in its insertion geometry by driving the device array 102 forward relative to the sheath 104. Depending on the forces provided by the drive mechanism used to actuate the device array, the articulating array may or may not be driven forward to its maximum depth. For example, a screw drive may be employed to drive forward the device array 102 into the insertion position shown in FIG. 3A. The travel of the device array 102 can be rigidly coupled to the travel of the screw drive. In some embodiments, the device array travels to a first insertion position shown in FIG. 3A. The device array 102 can then be articulated into an installed geometry, which in some examples results in the articulating array moving forward relative to the device and/or sheath 104. In some implementations, the connection at the screw drive can be configured to allow for forward travel by the articulating array 102 during subsequent articulation. In other embodiments, the screw drive can also be configured to travel forward responsive to the articulation of the articulating array 102 during transition from the insertion geometry to the installed geometry.

In some examples, the connection between a screw drive can include a compliant element, such as a spring, between the screw drive and an internal central support member. The spring transmits force from the screw drive to the device array, so that if the deployment of the device array is unrestricted, the articulating array will deploy normally. Alternatively, in the event that the end of the articulating array is restricted, the spring can absorb the screw's travel, allowing the articulating array to rest at a sub-maximum deployment without heavy stress. Further the compliant element can permit the articulating array to move forward further into, for example, the patient's uterus responsive to articulation of the articulating array. In one example, the articulating array rolls into the installation geometry during expansion of the plurality of chambers.

The process of rolling the articulating array into the installation geometry can cause the articulating array to be positioned more securely inside the uterus by moving further into the uterine cavity. In some examples, the compliant element can permit the additional movement of the articulating array. In other embodiments, the device can be configured to permit the articulating array to move freely during articulation of the articulating array. Thus, the forward pressure exerted by the articulating array causes the articulating array and, for example, the screw drive to move forward.

In some aspects, the introduction of a compliant element to the screw drive allows for a simple drive mechanism that controls the insertion force that the articulating array is able to generate.

Functionally, a purpose of the articulating array of the intrauterine therapy application device is to position a conductive array constructed on the surface of array 102 into a deployed state. An RF source (e.g., RF generator 110) can be configured to deliver power to the conductive array on the surface of the articulating array. Responsive to input of power from the RF generator, heat can be generated that ablates the uterine lining. In some embodiments, the conductive array can be knit from elastic yarn, so a certain level of force is needed simply to spread the conductive array to the desired shape. In some examples, the force can be applied through expansion of the plurality of chambers. In other embodiments, the conductive array can be printed and/or constructed on the surface of the articulating array. The conductive array can be printed and/or constructed on the surface of the articulating array based on the installed geometry, thus when the articulating array is transitioned into an installed geometry the mesh on the surface of the articulating array can be positioned proximate to, for example, the patients uterine lining.

In addition to stretching and/or positioning the conductive array, the device 100 can be configured to overcome resistance encountered during transition from an insertion geometry to an installed geometry. For example, a pressure controller can be configured to increase pressure delivered to the plurality of chambers until the articulating array is configured in its installed geometry. In some settings, the intrauterine device is configured to limit the pressure applied to the plurality of chambers, and thereby prevent injury during a procedure, as described in greater detail below.

According to one approach, improving the durability and flexibility of the articulating array includes constructing the articulating array of a high elongation material (e.g., silicone, rubber, etc.) to enable the articulating array to be softer, more compliant/resilient, and/or better form fitting so that the articulating array can endure significant stress and strain, and even displacement and/or deformation and still return to an original configuration. This approach enables reduction in the size of the articulating array and consequently the sheath and intrauterine device required. Further the strength of the high elongation materials can be configured to supply the desired pressure for properly positioning of the conductive array. In some embodiments, an intrauterine device can include a vacuum and/or pump for supplying increasing pressures to the plurality of chambers. In other embodiments, pressured air or fluid can be driven into the plurality of chambers by manual operation.

Referring again to the Figures, a detailed description of various embodiments of such an intrauterine therapy application device and array structure will now be discussed. FIG. 1 is a side elevation view of an intrauterine therapy application device 100 with an articulating array 102 in a retracted position inside a hollow sheath 104. The intrauterine therapy application device 100 includes a handle 106, and is coupled via a cable 120 to a radiofrequency signal generator 110 and via a tube 128 to a vacuum/pump source 112. The radiofrequency generator 110 generates an electrical signal, for example a radiofrequency signal, and transmits it to a conductive array disposed on the articulating array 102 through the cable 120, which is ultimately coupled to the conductive array through the handle 106. The vacuum/pump source 112 can be connected to the handle 106 at the port 122. In some embodiments, vacuum/pump source 112 can create suction for removal of ablated tissue. In other embodiments, vacuum pump source can be connected to a plurality of tubes (e.g., 128) connected to one or more ports (e.g., 122) to control a pressure delivered to an articulating array 102 including a plurality of expansion chambers. According to one feature, the distal end 104a of the sheath 104 of the intrauterine therapy application device 100 is configured to be inserted into a patient's cervix.

Figure 2:
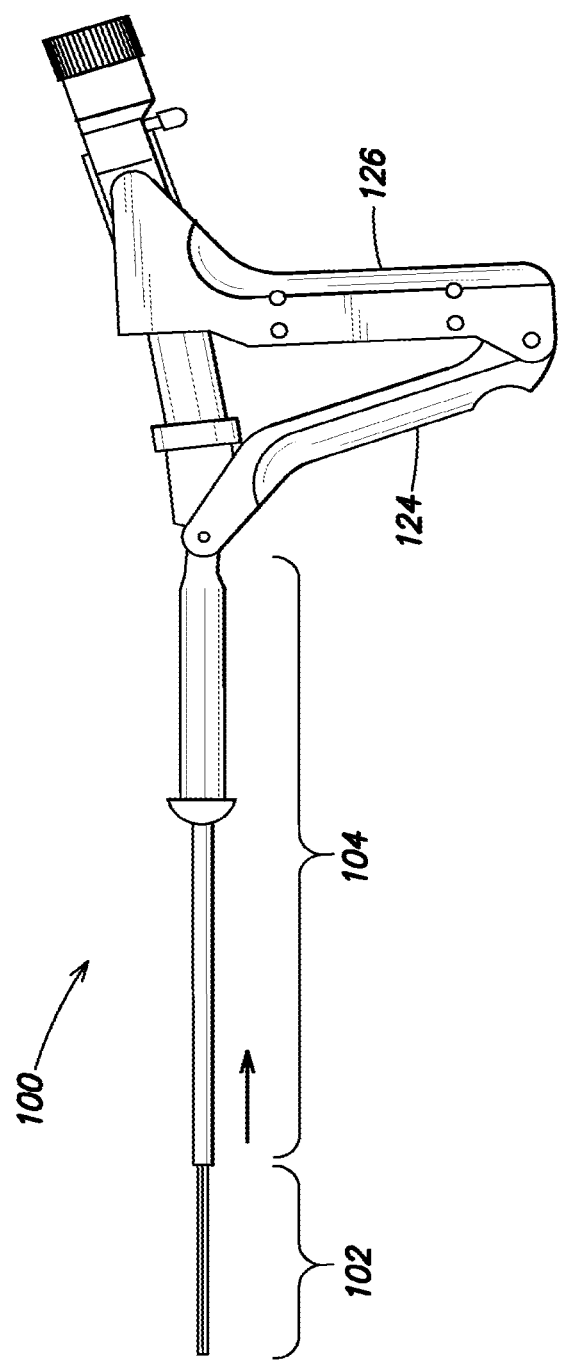
FIG. 2 is a side elevation view of the intrauterine therapy application device of FIG. 1, showing the articulating array according to aspects of the disclosure.

The handle 106 includes a distal grip 124 and a proximal grip 126. During use, the proximal grip 126 is squeezed toward the distal grip 124, to cause the articulating array 102 to extend out from the sheath 104, as shown in FIG. 2, for example, by operation of drive shaft 108. As shown in FIG. 2, the articulating array 102 is extended out from the sheath 104 in an insertion geometry or collapsed position as shaft 108 is driven forward. As the articulating array 102 extends out from the sheath 104 in the insertion geometry or collapsed position, it may be configured to begin transitioning into the installed geometry, as shown in the perspective view of the deployed array illustrated in FIG. 3B. In some embodiments, operation of proximal and distal grips can be configured to force air and/or liquid into the plurality of expansions chambers increasing the pressure in the plurality of expansion chambers causing the chambers to expand into the installed geometry as the articulating array 102 is fully extended from the sheath 104. In some embodiments, shaft 108 can be configured to operate on a fluid or air bladder and shaft 108 can be configured to apply pressure on the bladder when the proximal grip 126 is squeezed toward the distal grip 124. The increase in pressure can be communicated to the articulating array 102 causing it to extend out from the sheath 104 and subsequently to transition into an installed geometry.

In other embodiments, the articulating array 102 may be configured to extend out from the sheath 104 until it reaches a preconfigured position. Once the articulating array 102 reaches the preconfigured position, a pressure controller can be operated to increase pressure in the plurality of expansion chambers (e.g., 150, FIG. 3A) thereby articulating the articulating array into an installed position.

In some embodiments, the preconfigured position can be set on the intrauterine device manually, for example via a dial 129, such as to accommodate a specific patient's anatomy. In one embodiment, the dial 129 can control a length of shaft 108. By manipulating the dial 129 an operator can lengthen or shorten shaft 108. Lengthening and shortening the shaft 108 can be configured to alter the insertion distance travelled by array 102. In other implementations, lengthening and shortening of the shaft 108 can be configured to alter a pressure delivered to the plurality of chambers, which can be configured to control insertion attributes (e.g., insertion depth, insertion geometry, etc.)

In other examples, a dial can also be configured to control a valve that permits a fluid (gas and/or liquid) to flow into the plurality of expansion chambers, so that in response to reaching the preconfigured position, the valve may open and pressurized fluid may be delivered to the plurality of expansion chambers. In other embodiments, the dial can control the activation of a switch or sensor that indicates the preconfigured position has been reached. The switch or sensor can control the opening of a valve that controls flow to the plurality of expansion chambers. In yet other embodiments, a pump or motor can be configured to deliver increased pressure to the plurality of expansion chambers once the preconfigured position has been reached. The switch and/or sensor can also be configured to deliver a control signal to the pump or motor that indicates that increased pressure can be delivered to the plurality of expansion chambers.

In other embodiments, the articulating array 102 and the pressure controller can be configured to extend the articulating array from the sheath 104 with selective pressure applied to one or more of the chambers of the articulating array, while maintaining the plurality of expansion chambers in the insertion geometry. Rather than use a screw drive, for example, the articulating array 102 can be configured to extend outward from the sheath 104 with increased pressure applied to one of more of the plurality of expansion chambers. In some implementations, the plurality of expansion chambers can be arranged in a linear arrangement. In some embodiments, the pressure controller and the plurality of expansion chambers can be configured to deliver an increased pressure to one of more of the plurality of expansion chambers to extend the articulating array, and once the articulating array is extended from the sheath in the insertion geometry, the pressure controller can be configured to further selectively provide increased pressure to the one or more of the plurality of expansion chambers to articulate the articulating array into an installed position.

FIG. 3A is a perspective view of a portion of an intrauterine therapy application device array in a deployed position, according to an embodiment of the disclosure. The articulating array 102 includes a plurality of expansion chambers 150 and an external surface 151. The articulating array 102 can be constructed and arranged of a contiguous material and configured to retain an insertion geometry when the plurality of expansion chambers 150 are not under pressure.

In some embodiments, the plurality of expansion chambers are constructed to include respective seals, and/or valves that enable selective inflation of the plurality of expansion chambers and/or facilitate transition of the articulating array between the insertion and installed geometries. The plurality of expansion chambers can be constructed and arranged to have a first geometry when not inflated or having a pressure less than a threshold and at least a second geometry when fully inflated or having a pressure greater than a threshold. In some embodiments, the articulating array can be configured to achieve various positions in between the insertion geometry and installed geometry by varying the pressure within select of the plurality of expansion chambers. In some implementations, the plurality of expansion chambers are constructed and arranged of pneumatic networks ("pneunets") of channels in elastomers. With such an arrangement, selective increases in pressure can be supplied to the plurality of expansion chambers, for example, through the pneumatic networks. With this arrangement, it is understood that the delivery of selective increases in pressure to the plurality of expansion chambers can be used to provide rigidity to the articulating array, for example, to restore the articulating array to its insertion geometry. For example, it is understood that the articulating array can be deformed from an insertion geometry upon advancement from the sheath due to, for example, gravity or the plurality of expansion chambers encountering some internal resistance to the advancement of the articulating array. With such arrangement, a controller can be configured to selectively deliver increases in pressure to one or more of the plurality of expansion chambers to overcome gravity or such deformation in the articulating array so as to restore the articulating array to its insertion geometry.

The articulating array can be connected to a drive shaft or an air bladder as discussed above, at 152. The spacing shown between 152 and the end of the sheath 104 can be configured based on measurements taken of a patient's uterus. In some further embodiments, the spacing shown between 152 and the end of the sheath 104 can provide for some variation in a deployment distance. The connection at 152 is configured to provide a telescoping arrangement whereby the articulating array 102 is extended outward from the sheath 104 when operated.

The articulating array 102 can include channels at 153, some can be constructed and arranged to extend the length of the articulating array 102. Channels 153 are configured to deliver fluid to the plurality of expansion chambers at 150. For example, vacuum/pump 112 can force fluid into the plurality of expansion chambers 150, increasing fluid pressure within the expansion chambers. In another example, operation of the handle (e.g., 124-126) can be configured to deliver increased pressure to the plurality of expansion chambers.

As shown in FIG. 3A, the articulating array 102 extends outward from the sheath 104 in an insertion geometry defined by the outer surface 151 and shape of the plurality of expansion chambers 150. In other embodiments, additional expansion chambers can be constructed and arranged within articulating array 102, and in some further embodiments, fewer expansion chambers can be constructed and arranged within articulating array 102.

Referring back to FIG. 3A, according to one embodiment, the articulating array can include one or more hollow elongate tubes (not shown). When suction is applied to the uterine cavity, for example from the suction source (e.g., 112 shown in FIG. 1), fluid, vapor, liquid, and/or tissue may be suctioned through the one or more hollow elongate tubes, away from the patient.

FIG. 3B is a perspective view of the portion of an intrauterine therapy application device in a installed position. As shown, the articulating array 102 and a plurality of expansion chambers at 160 have been expanded to cause the articulating array to transition from an insertion geometry (FIG. 3A) to an installed geometry (FIG. 3B). According to some embodiments, the articulating array can also include a conductive array (e.g. FIG. 3C, 170) on an outer surface 161 of the articulating array 102. The conductive array can be, for example, printed on the outer surface 161 of the articulating array 102 so that the conductive array is proximate to a patient's uterine lining when the articulating array 102 is in an installed geometry (FIG. 3B). The conductive array may be knitted from a nylon and spandex knit and plated with gold, silver, or another conductive material. The conductive array can be configured to be conformable, permeable, and to carry current. In some embodiments, the conductive array can be attached to the articulating array at its outer surface 161. For example, strands of thread may be connected to the outer surface 161 of the articulating array 102. The strands of thread can be constructed of nylon. In some examples, the strands of thread forming the conductive array can be sewn into the articulating array 102 at the outer surface 161.

In other embodiments, conformable metal filaments can be printed directly on the outer surface of the articulating array 102. In some other embodiments, metal filaments (e.g., gold, silver, or another conductive material) can be attached to the outer surface of the articulating array 102. In further embodiments, other filaments (e.g., non-metal) to carry current can be printed and/or attached to the outer surface of the articulating array 102. The articulating array may be connected to a drive or a first expansion chamber at 162. The connection at 162 can be configured to allow some variability in an insertion distance traveled by the articulating array 102. In other embodiments, the connection 162 can travel further out from sheath 104 as the articulating array 102 transitions from an insertion geometry into an installed geometry.

The conductive array can be configured to carry current. Shown in FIG. 3C is an example conductive array disposed on the surface of an articulating array 102. Internal wires 172A and 172B can be configured to deliver current to the conductive array from, for example and RF source (e.g., RF 110, FIG. 1). The amount of current delivered to the conductive array can be configurable according to a geometry of the installed articulating array 102 and/or the conductive array disposed on its surface. In one example, the installed geometry of the articulating array 102 is approximately triangular. For the triangular geometry the power delivered can be calculated based on a desired power density, which can be determined from power divided by the surface area to which power is being delivered. Other geometries can require differing amounts of current to be delivered to the conductive array, for example, based on the surface area of the other geometry. As discussed, the differing amount of current can be controlled by an RF source 110 connected to a conductive array.

Figure 3D:
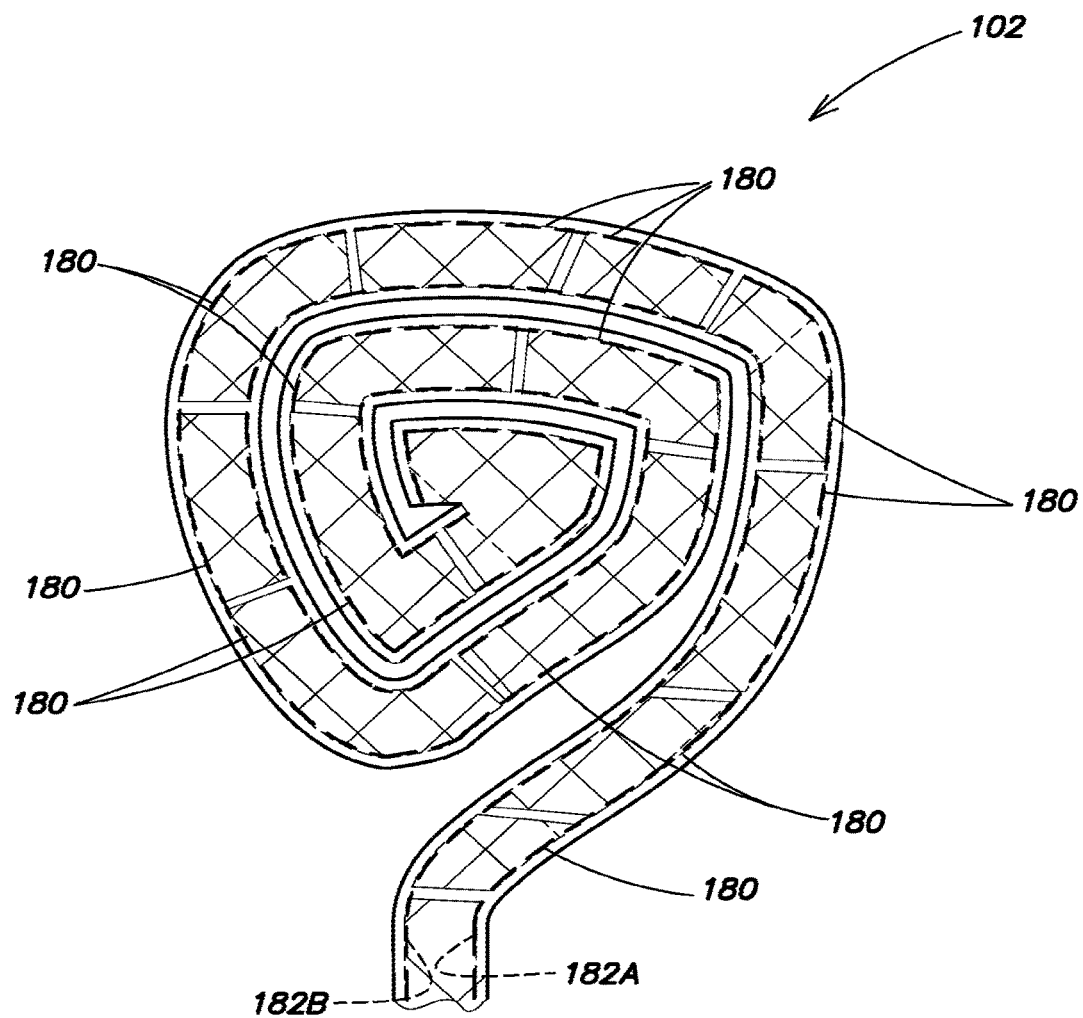
FIG. 3D is a perspective view of an embodiment of a portion of an intrauterine therapy application device with an articulating array showing a conductive array according to aspects of the disclosure.

Conductive arrays can be constructed and arranged on an outer surface of an articulating array 102 in a variety of structures. FIG. 3D illustrates an example conductive array constructed and arranged of a plurality of mesh portions shown at 180. Each mesh portion can be printed on a portion of an outer surface of the articulating array 102. Each mesh portion can be connected to wires 182A-B which can be connected to an RF source to supply current to each mesh portion. As discussed, the conductive array may be knitted from a nylon and spandex knit and plated with gold, silver, or another conductive material. Each mesh portion may also be knitted from a nylon and spandex knit and plated with gold, silver, or another conductive material. In other embodiments, filaments (e.g., metal, gold, silver, or another conductive material) can be printed on the outer surface of an articulating array 102 to form each mesh portion at 180. Once positioned, current can be supplied to each mesh portion to perform an ablation procedure on a patient's uterine lining.

In some embodiments, the articulating array can be fabricated without a conductive array. For example, in embodiments without a conductive array, the uterine lining could be ablated using hot or cold fluid introduced into the plurality of expansion chambers. In one implementation, refrigerants can be introduced into the articulating array to ablate the uterine lining. The refrigerants can include, for example, liquid nitrogen and nitrous oxide, among other options. In some embodiments, the articulating array can be fabricated with the plurality of expansion chambers constructed to position the articulating array in optimal communication with the uterine lining of a patient. According to some embodiments, the articulating array can include additional channels for delivering hot or cold fluid proximate to the surface of the articulating array in contact with the uterine lining. In other embodiments, the hot or cold fluid can be introduced into the plurality of expansion chambers to ablate the uterine lining.

Figure 4A:
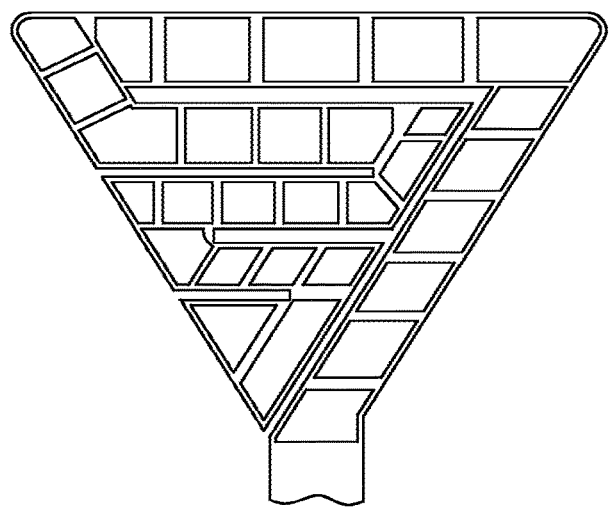
FIGS. 4A-C illustrate installed geometries of embodiments of an articulating array according to aspects of the disclosure.
Figure 4B:
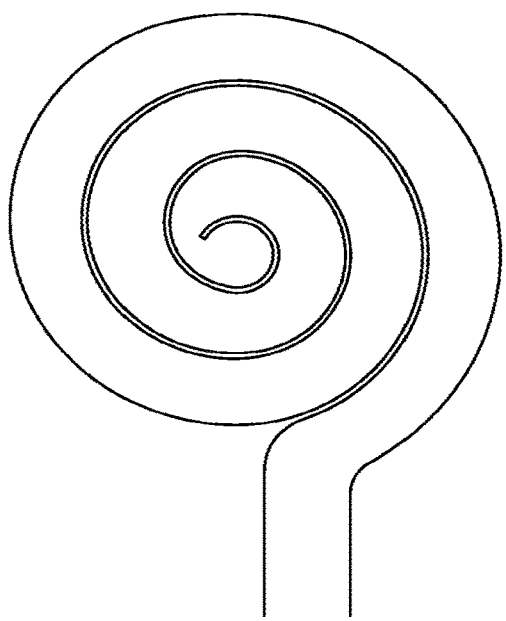
Figure 4C:
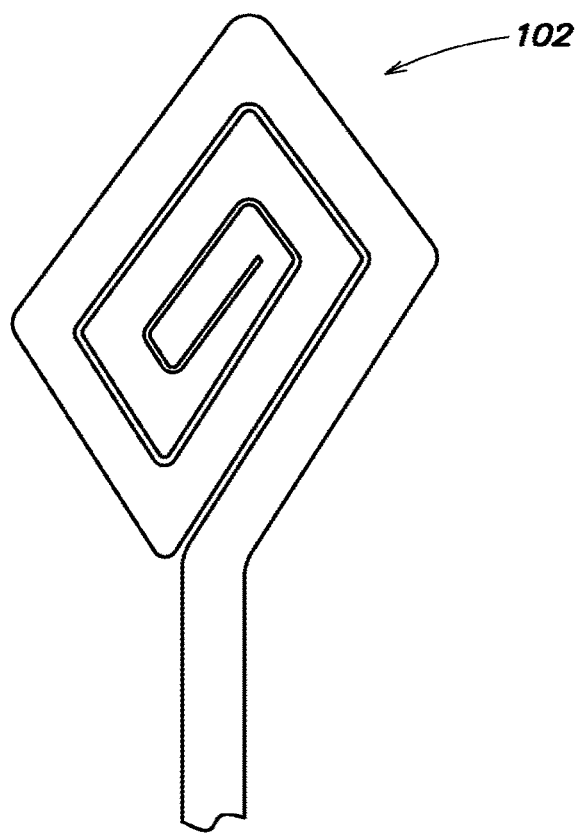

It is appreciated that several properties of construction of the articulating array (e.g., 102) can be controlled to adjust stiffness and create a flexure with a plurality of expansion chambers, each having a variety of stiffnesses and expansion geometries. Once the plurality of expansion chambers are expanded the articulating array can take on a variety of installation geometries. Shown in FIGS. 4A-C are example installation geometries that can be obtained by expanding a plurality of expansion chambers within an articulating array (e.g., triangular FIG. 4A, circular FIG. 4B, and diamond FIG. 4C). For example, selected manufacturing processes can be used to alter the elasticity provided by different portions of the articulating array (e.g., combining different materials, using different thicknesses for dimensions of respective expansion chambers, etc.). The manufacturing processes can be used selectively on different areas of an articulating array to create an articulating array of a plurality of expansion chambers having different elasticities in different areas of the articulating array. In some further examples, the articulating array may be constructed of multiple materials, each material having a different modulus of elasticity. In a further example, the cross-sectional profile of each expansion chamber, such as the thickness and/or width of the chamber, may be adjusted to create an expansion chamber having an expanded geometry that forces the articulating array to take on an installation geometry when the individual chambers comprising the articulating array are expanded.

It is appreciated that adjusting the cross-sectional profile of one or more of the expansion chambers can alter the geometry obtained by a given embodiment of the articulating array, when the plurality of expansion chambers are being expanded. In further embodiments, other methods and characteristics may be used to control the stiffness of certain portions of an articulating array so as to alter the geometry and/or overall volume obtained by the articulating array. Additionally, varying pressure can be selectively applied to one or more of the plurality of expansion chambers to trigger articulation of the articulating array in a desired manner during transition from the insertion geometry to the installed geometry. In one embodiment, the pressure controller and the articulating array can be selectively controlled to transition to one or more intermediate positions of the articulating array from an insertion geometry (e.g., FIG. 3A) to the installed geometry (e.g., shown in FIGS. 4A-4C) much like a frond unfolds, except in reverse. With such an arrangement, the shape and/or overall volume that the articulating array takes in the one or more intermediate positions during the transition from the insertion geometry to the installed geometry can be controlled through the selective inflation of the plurality of expansion chambers. It is appreciated that with such an arrangement, the the shape and/or the overall volume of the articulating array in the intermediate positions between the insertion geometry and the installed geometry can be controlled to minimize the overall volume occupied by the articulating array during the transition, such as to yield to neighboring tissue. This may be desirable, for example, so as to increase patient comfort during the transition from the insertion geometry of the articulating array to the installed geometry of the articulating array.

Figure 6:
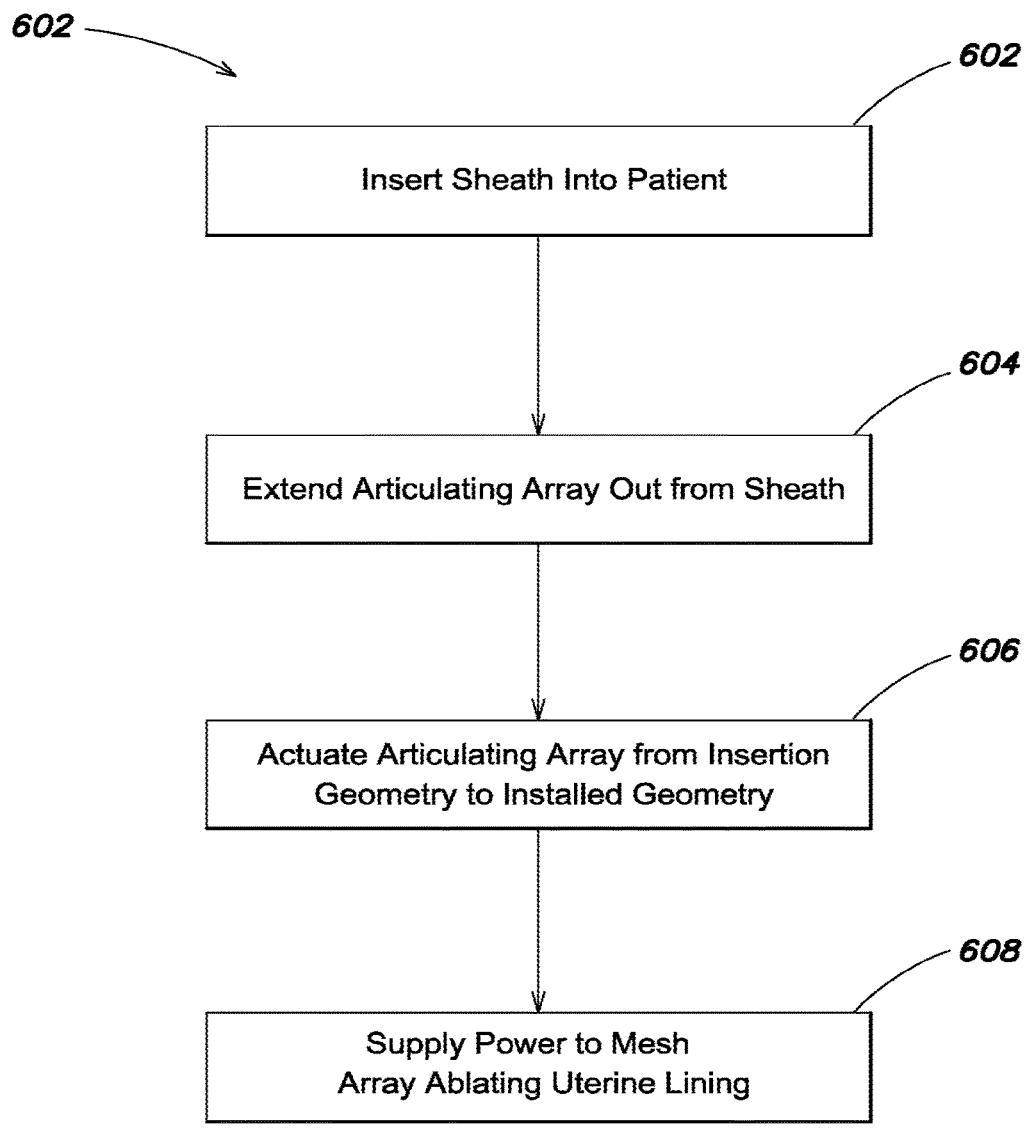
FIG. 6 illustrates a process for positioning an intrauterine device for an ablation procedure according to aspects of the disclosure.

In FIG. 6 illustrated is an example process for ablating the uterine lining of a patient using a therapy device having an articulating array. Process 600 begins at 602 with an operator inserting a sheath of the therapy device into the cervix of the patient. Once the sheath has been positioned, the articulating array of the device is extended outward from the sheath at 604. Pressured can be delivered to the articulating array, for example, by increasing fluid pressure delivered to the articulating array through the therapy device. The increased pressure results in actuation of the articulating array. At 606 the articulating array transitions from an insertion geometry to an installed geometry within the uterus of the patient. Once the articulating array has been positioned within the patient's uterus, a conductive array on the articulating array is also position proximate to the patient's uterine lining. At 608, power can be supplied to the conductive array ablating the uterine lining of the patient. In some examples, power can be delivered by an RF source connected to the therapy device. In some further examples, the RF source can be managed by a controller. The controller can also be configured to mange and/or monitor pressure and temperature during the procedure. The controller can be configured to alter pressure or power delivered in order to insure patient health and safety.

Figure 5:
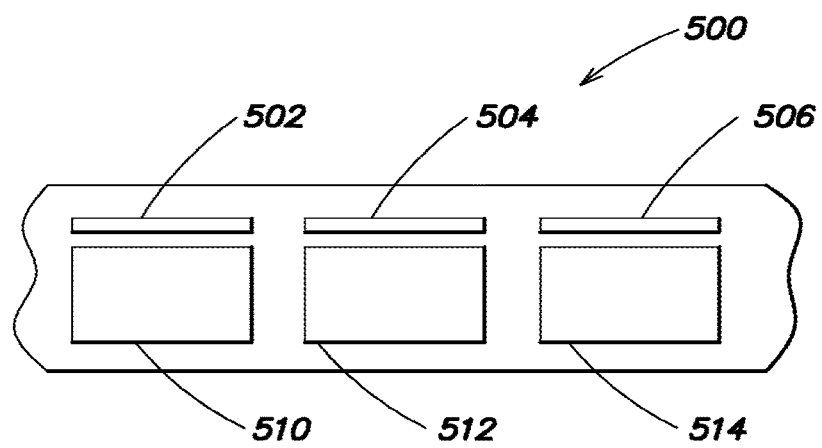
FIG. 5 illustrates examples of expansion chambers included in an articulating array according to aspects of the disclosure.

Shown in FIG. 5 is a portion of an articulating array 500 including expansion chambers 510, 512, and 514. Increased pressure delivered to chambers 510-514 can result in the portion of the articulating array taking on an installed geometry defined by the elasticity of the chambers. In some embodiments, the articulating array can be fabricated to include a plurality of sensors 502, 504, and 506. The plurality of sensors can be disposed on an exterior surface of the articulating array or can be embedded within the articulating array structure. In some examples, pressure sensors can be configured to detect pressure with the plurality of chambers. In other examples, sensors (e.g., 502-506) can be configured to determine a change in dimension of the plurality of chambers. The change in dimensions can be communicated to a pressure controller. The pressure controller can be configured to determine that, for example, the pressure supplied has resulted in a smaller change in configuration than expected. Smaller changes in configuration can be associated with resistance, prompting an increase in pressure delivered to the plurality of chambers and/or an articulating array. Proximity sensors can also be employed to assist in deployment and positioning of an articulating array. In one example, strain gauges can be included in the plurality of sensors. The strain gauges can provide information to a controller to establish that the articulating array has or has not reached an installed position. Further, temperature sensors can be constructed within and/or on the surface of the articulating array and temperatures applied to the patient, for example, by current through a conductive array can be monitored to insure the temperature remain below a safe operating temperature. Other sensors can also be fabricated on or in the articulating array. According to some embodiments, sensor information can be communicated to a controller. The controller can be configured in some embodiments to respond to the sensor information automatically, or in other embodiments to provide indications to an operator regarding the sensor information. In further embodiments, the controller can be configured to respond automatically and report to various operators. For example, sensors can signal the controller to turn off portions of a conductive array on non-expanded portions of the articulating array to prevent electrical shorts, among other options.

Figure 7:
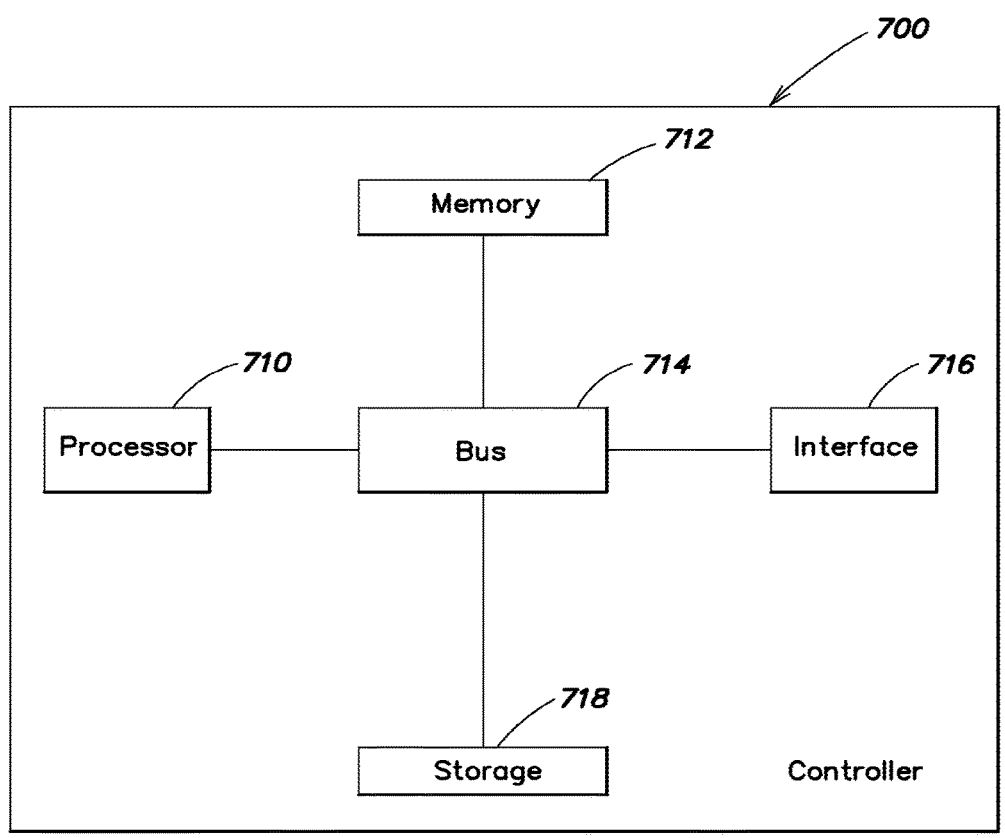
FIG. 7 is a block diagram of controller according to aspects of the disclosure.

Shown in FIG. 7 is an example controller which can be configured to, for example, regulate pressure delivered to an articulating array. In other embodiments, the controller can receive sensor information from an intrauterine therapy application device. The controller can be configured to process the information and act on the intrauterine therapy application device according to the received information. For example, if the sensor information indicates that the articulating array has not reached an installed geometry, increased pressure can be delivered to the device to achieve the installed geometry. In one embodiment, the controller can be connected to a vacuum/pump and control the pressure supplied to the device.

In another example, the controller 700 can be configured to manage power delivered to an intrauterine therapy application device. In some examples, the controller can be configured to receive sensor information on position and/or temperature. The controller can be configured to limit power delivered from, for example, an RF source to the conductive array until the articulating array is in an installed position. Further, the controller can also be configured to maintain procedure appropriate temperature being applied to the patient. If a threshold temperature is exceeded, the controller can be configured to reduce or cease power supplied from the RF source to the conductive array.

As discussed, FIG. 7 shows an example block diagram of the controller 700, which can be implemented as a computer system, in which various aspects and functions in accordance with the present disclosure may be practiced. The controller 700 may include one or more computer systems connected via a network. The computer systems may include mobile computing systems displaying user interfaces for interacting with the functions and/or sensor information provided by the controller (e.g., laptops, tablets, and other mobile devices). The user interfaces can be configured to allow an operator to make adjustments to the operation of the flexible array during a procedure.

Various aspects and functions in accord with the present disclosure may be implemented as specialized hardware or software executing in one or more computer systems including the controller 700 shown in FIG. 7. As depicted, the controller 700 includes a processor 710, a memory 712, a bus 714, an interface 716 and a storage system 718. The processor 710, which may include one or more microprocessors or other types of controllers, can perform a series of instructions that manipulate data. The processor 710 may be a well-known, commercially available processor such as an Intel Pentium, Intel Atom, ARM Processor, Motorola PowerPC, SGI MIPS, Sun UltraSPARC, or Hewlett-Packard PA-RISC processor, or may be any other type of processor or controller as many other processors and controllers are available. As shown, the processor 710 is connected to other system placements, including a memory 712, by the bus 714.

The memory 712 may be used for storing programs and data during operation of the controller 700. Thus, the memory 712 may be a relatively high performance, volatile, random access memory such as a dynamic random access memory (DRAM) or static memory (SRAM). However, the memory 712 may include any device for storing data, such as a disk drive or other non-volatile storage device, such as flash memory or phase-change memory (PCM). Various embodiments in accord with the present disclosure can organize the memory 712 into particularized and, in some cases, unique structures to perform the aspects and functions disclosed herein.

Components of the controller 700 may be coupled by an interconnection element such as the bus 714. The bus 714 may include one or more physical busses (for example, busses between components that are integrated within a same machine), and may include any communication coupling between system placements including specialized or standard computing bus technologies such as IDE, SCSI, PCI and InfiniBand. Thus, the bus 714 enables communications (for example, data and instructions) to be exchanged between system components of the controller 700.

Controller 700 can also include one or more interfaces 716 such as input devices, output devices and combination input/output devices. The interface devices 716 may receive input, provide output, or both. For example, output devices may render information for external presentation. Input devices may accept information from external sources. Examples of interface devices include, among others, keyboards, mouse devices, trackballs, microphones, touch screens, printing devices, display screens, speakers, network interface cards, etc. The interface devices 716 allow the controller 700 to exchange information and communicate with external entities, such as users and other systems.

Storage system 718 may include a computer-readable and computer-writeable nonvolatile storage medium in which instructions are stored that define a program to be executed by the processor. The storage system 718 also may include information that is recorded, on or in, the medium, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 710 or some other controller may cause data to be read from the nonvolatile recording medium into another memory, such as the memory 712, that allows for faster access to the information by the processor 710 than does the storage medium included in the storage system 718. The memory may be located in the storage system 718 or in the memory 712. The processor 710 may manipulate the data within the memory 712, and then copy the data to the medium associated with the storage system 718 after processing is completed. A variety of components may manage data movement between the medium and the memory 712, and the invention is not limited thereto.

Further, the invention is not limited to a particular memory system or storage system. Although the controller 700 is shown by way of example as one type of computer system upon which various aspects and functions in accord with the present invention may be practiced, aspects of the invention are not limited to being implemented on the computer system, shown in FIG. 7. Various aspects and functions in accord with the present invention may be practiced on one or more computers having different architectures or components than that shown in FIG. 7.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:

1. An intrauterine ablation device, comprising:
a sheath configured for transcervical introduction;
an articulating array slidably disposed within the sheath and comprising at least three serially disposed expansion chambers, the articulating array having an insertion geometry in which the expansion chambers are linearly aligned in a deflated configuration that may be inserted into a uterus through the sheath, and an installed geometry, in which the expansion chambers are inflated and are rolled into a non-linear configuration;
a conductive array disposed on a surface of the articulating array, wherein the conductive array is configured to contact uterine wall tissue when the conductive array is inserted into the uterus and transitioned to the installed geometry; and
a port configured to receive an inflation media, wherein delivery of the inflation media to the expansion chambers causes the articulating array to transition from the insertion geometry to the installed geometry.

2. The intrauterine ablation device of claim 1, the at least three serially disposed expansion chambers of the articulating array including at least first, second and third expansion chambers, wherein the second expansion chamber is disposed between the first and third expansion chambers, so that a proximal portion of the second expansion chamber is disposed adjacent to a distal portion of the first expansion chamber, and a distal portion of the second expansion chamber is disposed adjacent to a proximal portion of the third expansion chamber, wherein when the articulating array is positioned within a uterus via the sheath, and transitioned from the insertion geometry to the installed geometry, the respective first, second and third expansion chambers place the conductive array into contact with uterine wall tissue.

3. The intrauterine device of claim 1, wherein the conductive array comprises a mesh structure.

4. The intrauterine device of claim 1, wherein the articulating array further comprises a plurality of channels fluidly coupled to the expansion chambers for delivering and/or withdrawing the inflation media to the expansion chambers through the channels.

5. The intrauterine device of claim 1, wherein inflation of the expansion chambers causes the articulating array to transition from the insertion geometry into the installed geometry.

6. The intrauterine device of claim 1, wherein the installed geometry comprises a furled frond-like configuration.

7. The intrauterine device of claim 1, further comprising a contact sensor disposed on an outer surface of the articulating array.

8. The intrauterine device of claim 1, further comprising a strain gauge coupled to the articulating array.

9. The intrauterine device of claim 1, further comprising at least one sensor configured to sense the installed geometry of the articulating array.

10. The intrauterine device of claim 1, further comprising at least one inflation member having an inflation lumen fluidly coupled to the expansion chambers, with a proximal end of the inflation member configured for fluidly coupling the inflation lumen with a source of inflation media.

11. The intrauterine device of claim 1, further comprising a controller configured to control pressure within the expansion chambers so as to transition the articulating array between the insertion geometry and the installed geometry.

12. The intrauterine device of claim 1, wherein the installed geometry is defined by an elasticity of the expansion chambers.

13. The intrauterine device of claim 1, wherein the installed geometry is triangular, circular, or diamond-shaped.

* * * * *